(12) United States Patent
Eaton et al.

(10) Patent No.: US 9,381,307 B2
(45) Date of Patent: Jul. 5, 2016

(54) INJECTION DEVICE

(75) Inventors: Mark Eaton, Witney (GB); Toby Cowe, Oxford (GB)

(73) Assignee: OWEN MUMFORD LIMITED, Oxford (GB)

( * ) Notice: Subject to any disclaimer, the term of this patent is extended or adjusted under 35 U.S.C. 154(b) by 238 days.

(21) Appl. No.: 13/883,879

(22) PCT Filed: Nov. 8, 2011

(86) PCT No.: PCT/GB2011/052175
§ 371 (c)(1),
(2), (4) Date: Jul. 10, 2013

(87) PCT Pub. No.: WO2012/063061
PCT Pub. Date: May 18, 2012

(65) Prior Publication Data
US 2013/0281943 A1 Oct. 24, 2013

Related U.S. Application Data

(60) Provisional application No. 61/411,100, filed on Nov. 8, 2010.

(30) Foreign Application Priority Data

Nov. 8, 2010 (GB) .................................. 1018827.4

(51) Int. Cl.
*A61M 5/00* (2006.01)
*A61M 5/315* (2006.01)
*A61M 5/20* (2006.01)
*A61M 5/24* (2006.01)

(52) U.S. Cl.
CPC .............. *A61M 5/31583* (2013.01); *A61M 5/20* (2013.01); *A61M 5/24* (2013.01); *A61M 5/31553* (2013.01); *A61M 5/3156* (2013.01); *A61M 2005/2407* (2013.01); *A61M 2005/2488* (2013.01); *A61M2005/2492* (2013.01); *A61M 2207/00* (2013.01); *Y10T 29/49826* (2015.01)

(58) Field of Classification Search
CPC ............. A61M 2005/2407; A61M 2005/2488; A61M 2005/2492; A61M 5/20; A61M 5/24; A61M 5/31553; A61M 5/3156; A61M 5/31583
See application file for complete search history.

(56) References Cited

U.S. PATENT DOCUMENTS

| 5,104,380 | A | 4/1992 | Holman et al. | |
| 7,686,786 | B2 * | 3/2010 | Moller | A61M 5/14566 604/134 |
| 2008/0108953 | A1 | 5/2008 | Moser et al. | |
| 2010/0280460 | A1 * | 11/2010 | Markussen | A61M 5/2033 604/195 |

FOREIGN PATENT DOCUMENTS

| GB | 2 463 034 | 3/2010 |
| WO | 2007/063342 | 6/2007 |
| WO | 2008/020023 | 2/2008 |
| WO | 2008/116766 | 10/2008 |
| WO | 2009/007305 | 1/2009 |
| WO | 2010029043 | 3/2010 |
| WO | 2010/115670 | 10/2010 |

OTHER PUBLICATIONS

International Search Report dated May 9, 2012, corresponding to PCT/GB2011/052175.

* cited by examiner

*Primary Examiner* — Rebecca E Eisenberg
(74) *Attorney, Agent, or Firm* — Young & Thompson

(57) ABSTRACT

An injection device includes a housing (40) for containing a syringe or cartridge (14) of medicament; a rotary drive shaft (20) for being rotated by an adjustable preset amount to cause expression of a corresponding amount of medicament from the syringe or cartridge; a torsion drive spring (24) anchored at one end region relative to the drive shaft (20) and, at its other end region being secured to a fitting (44) adapted to non-rotatably engage a seat (48, 50) on the housing.

13 Claims, 11 Drawing Sheets

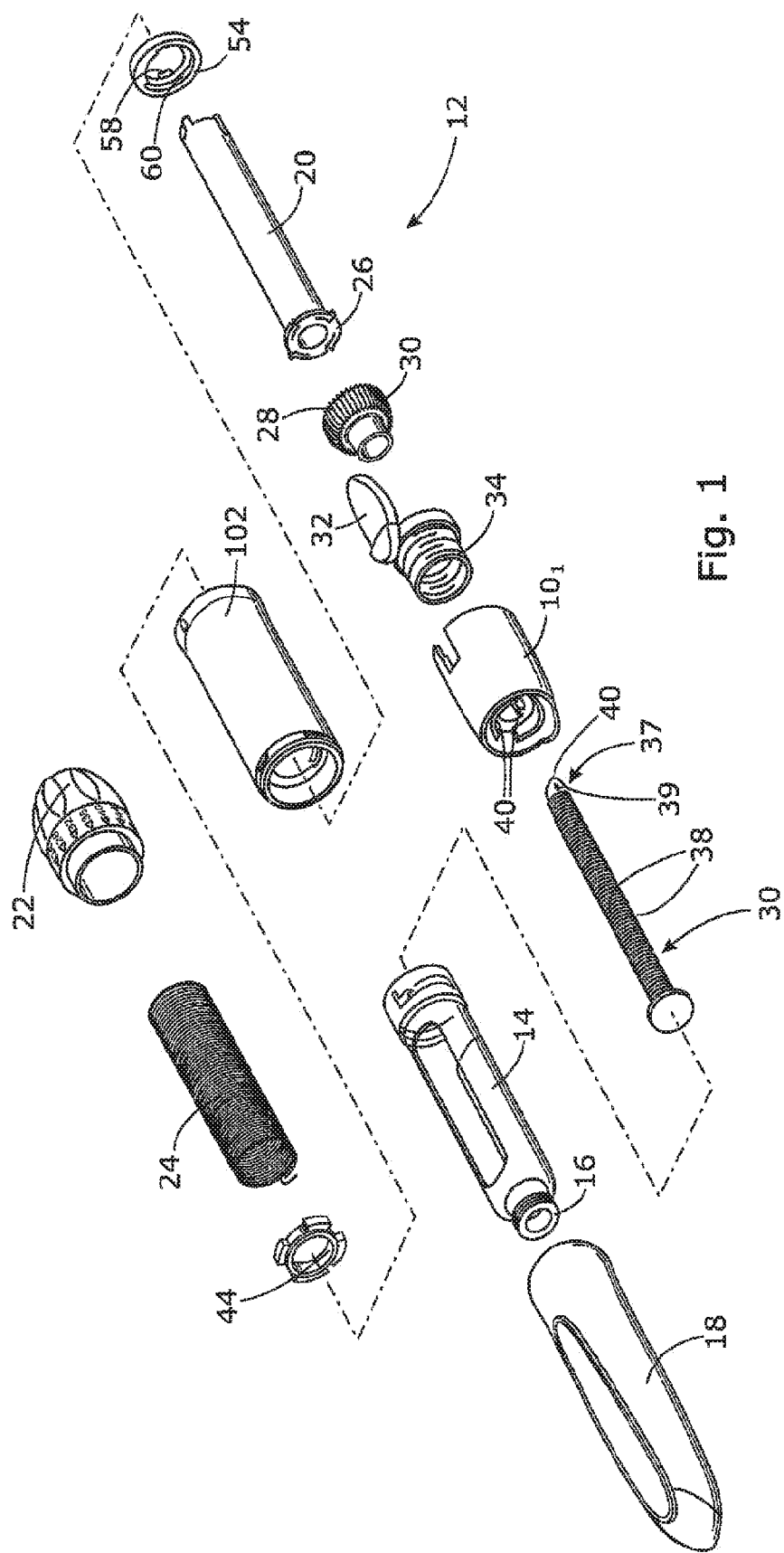

Figure 11:
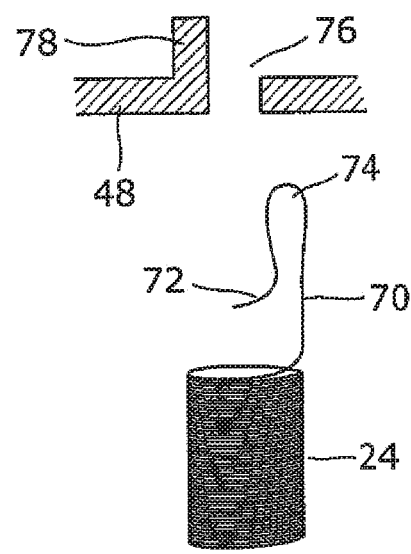

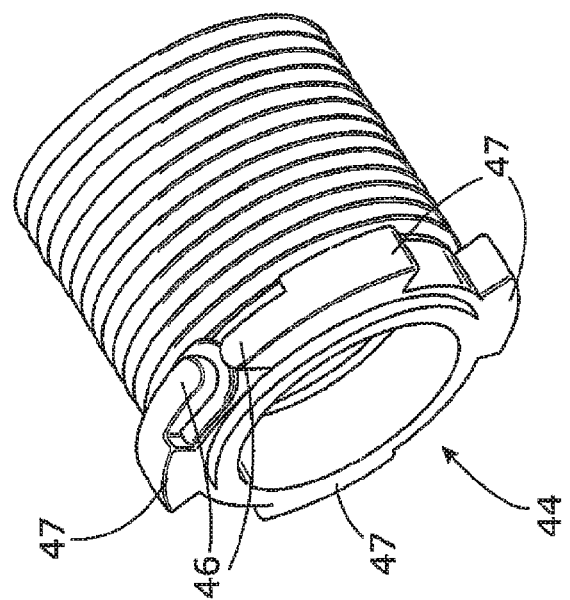
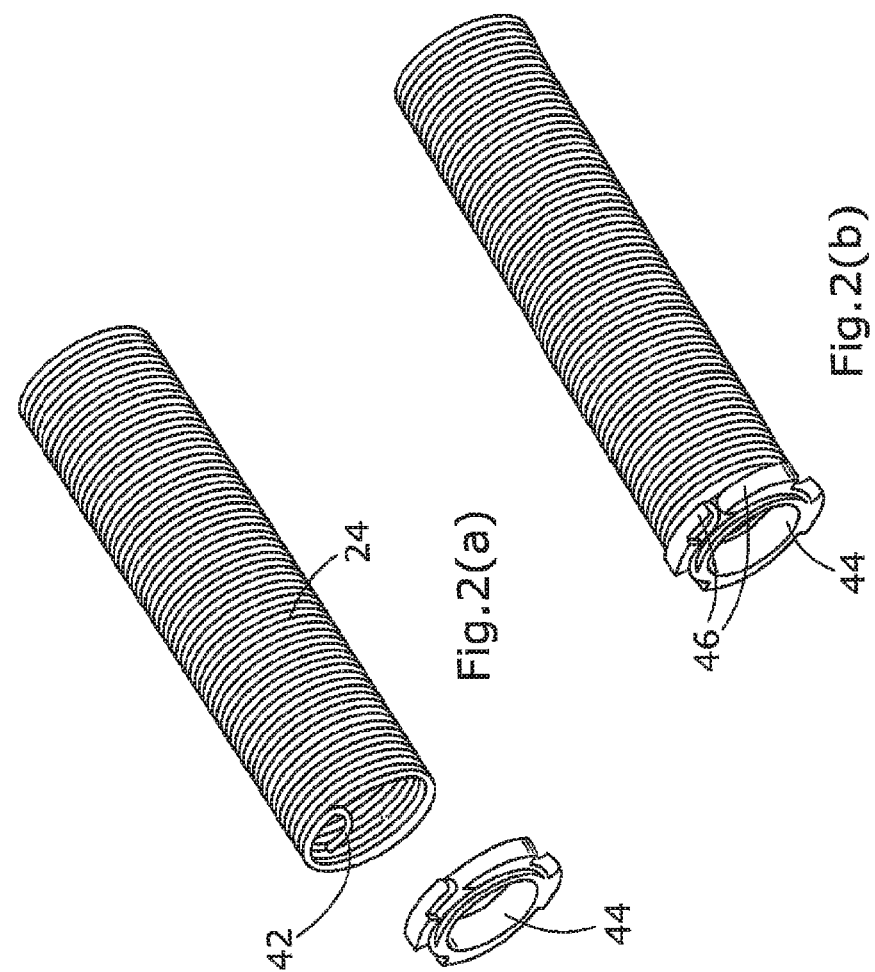

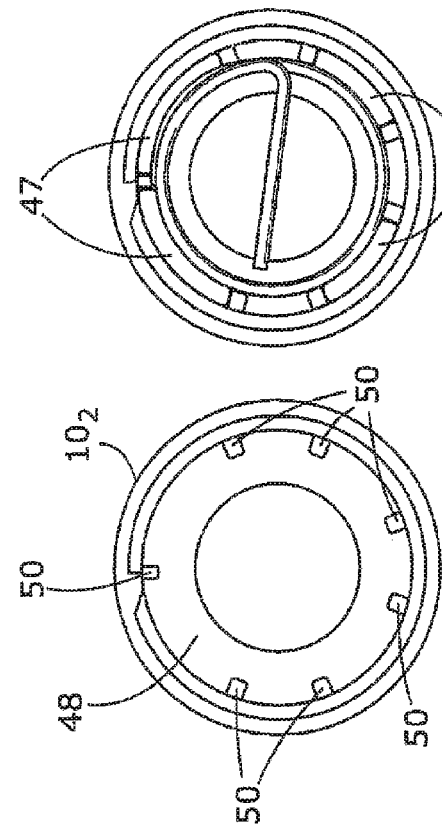
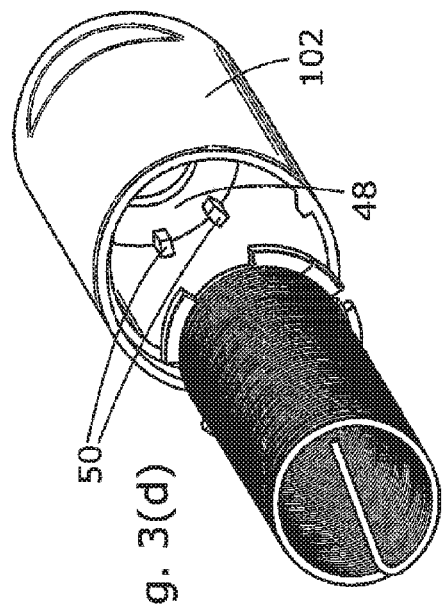
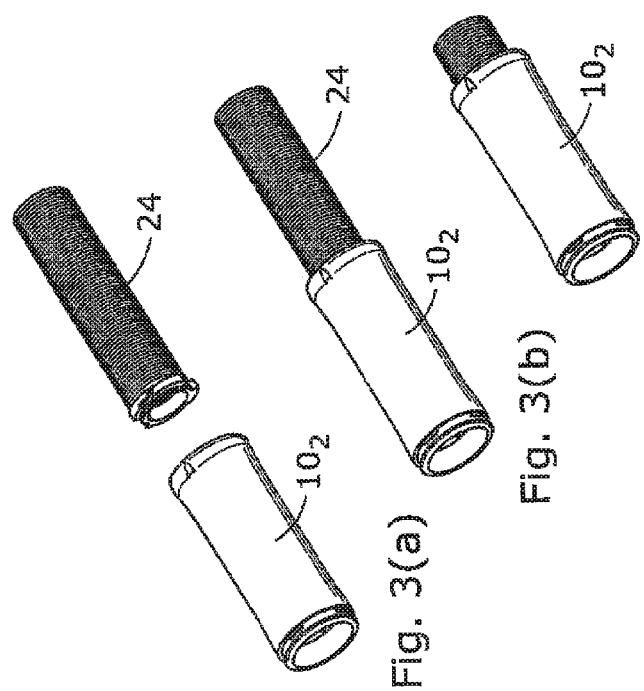

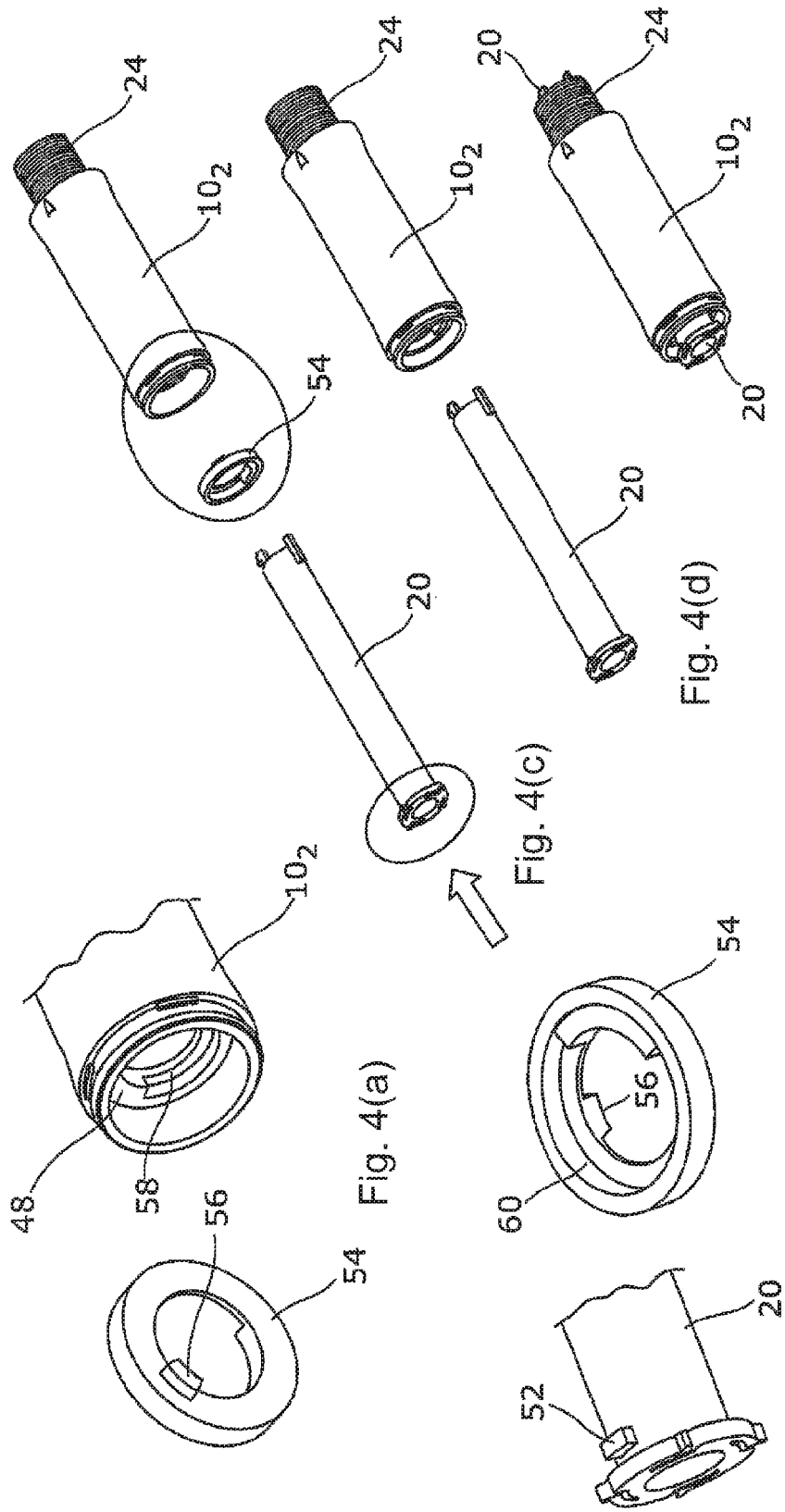

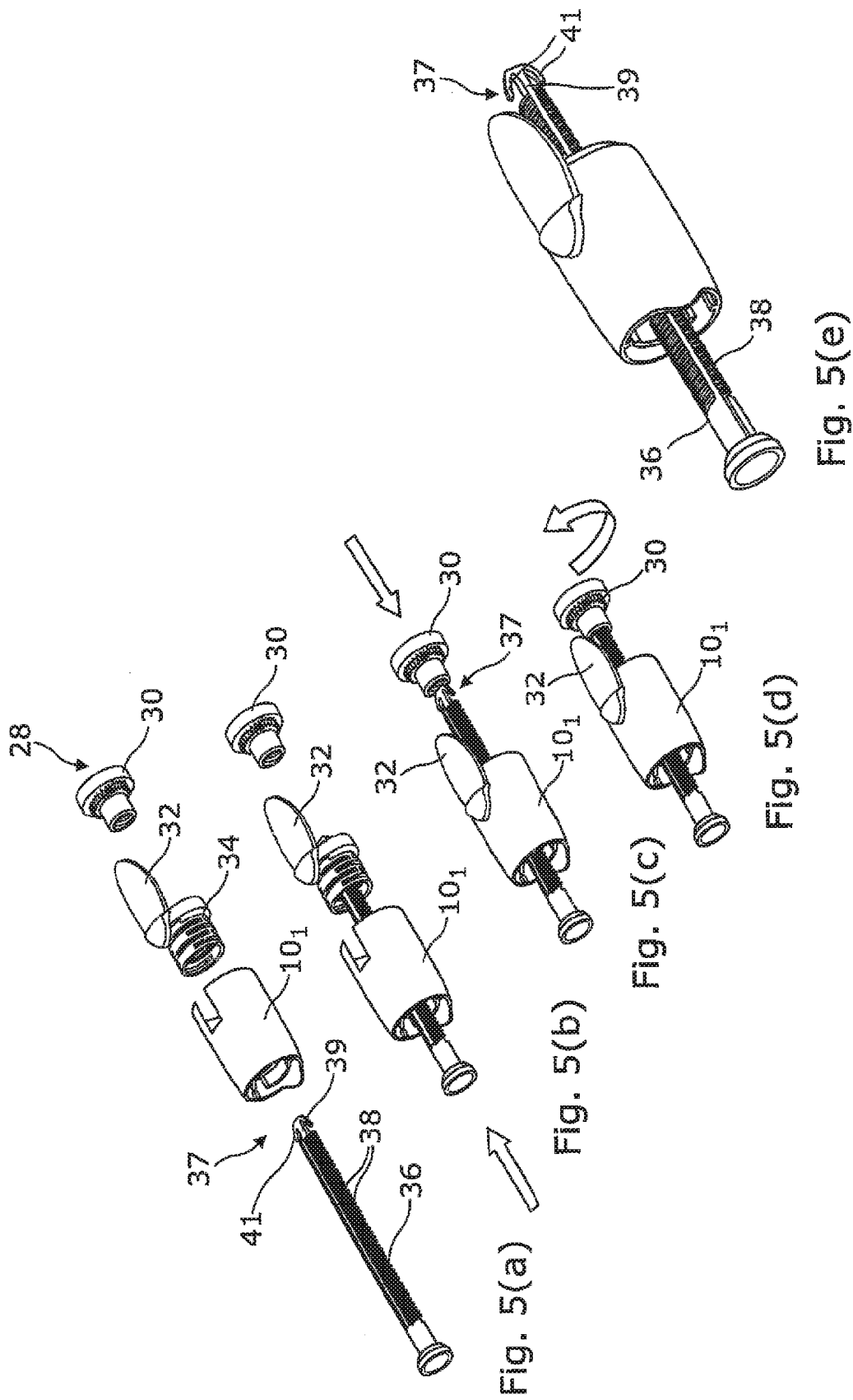

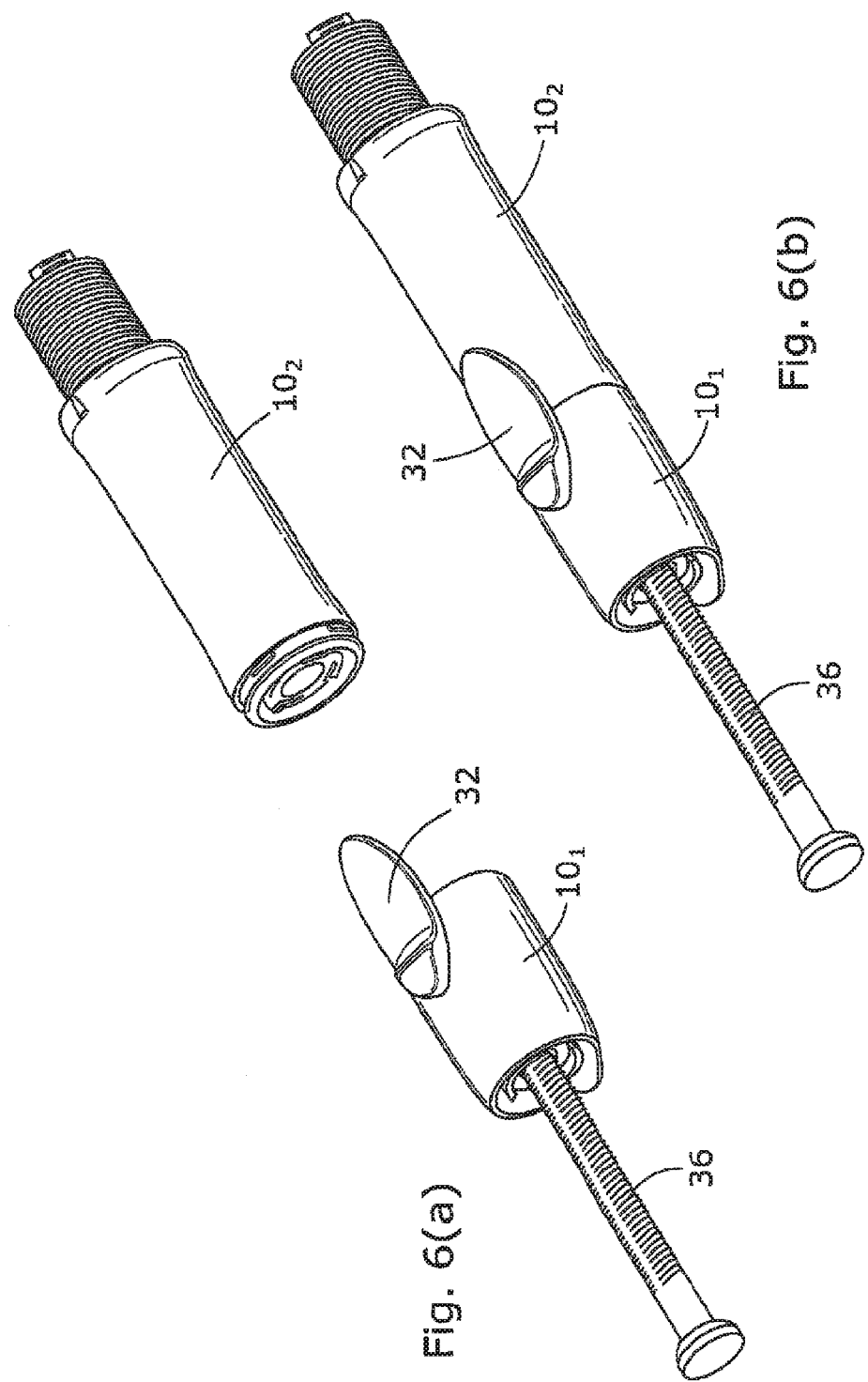

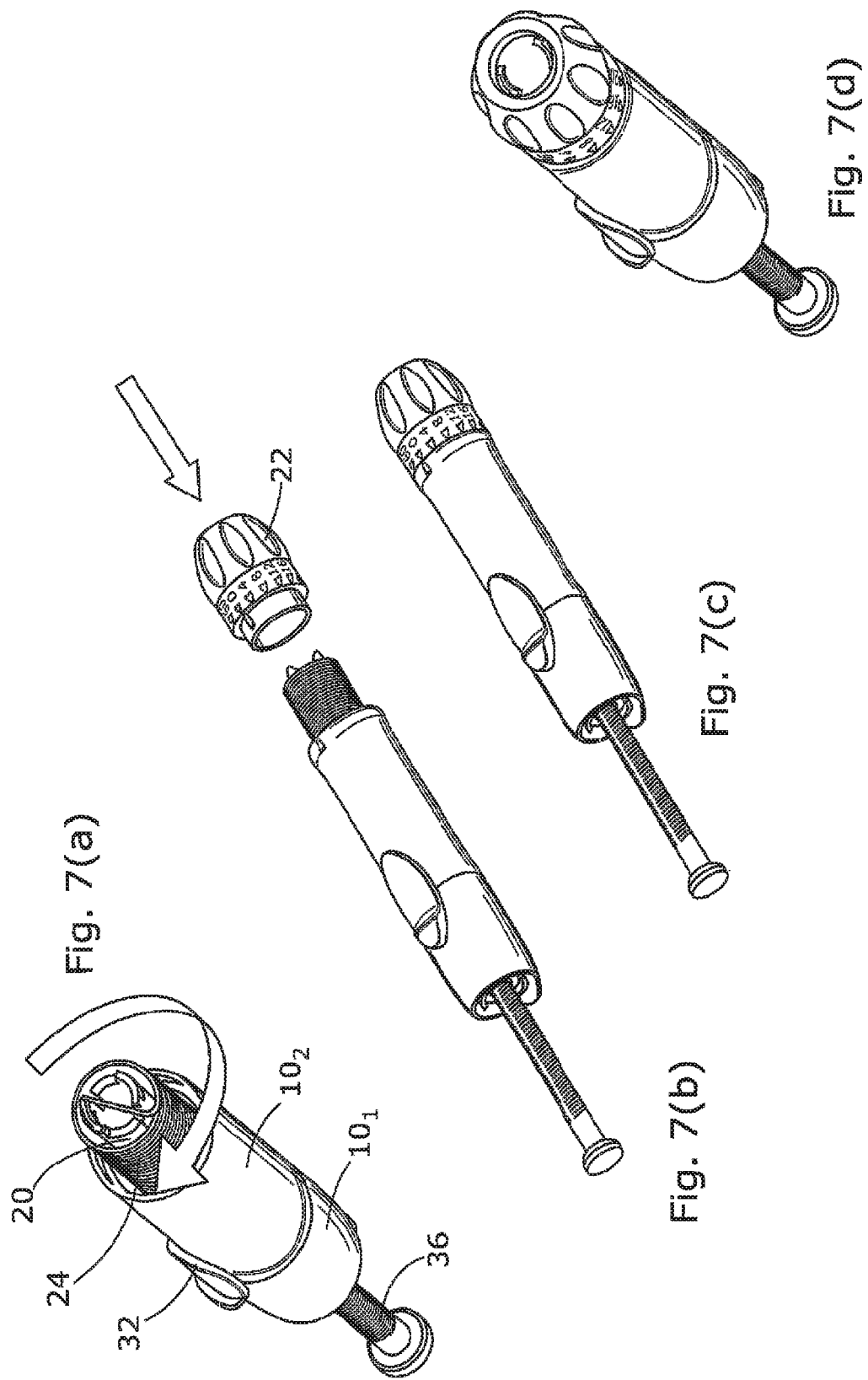

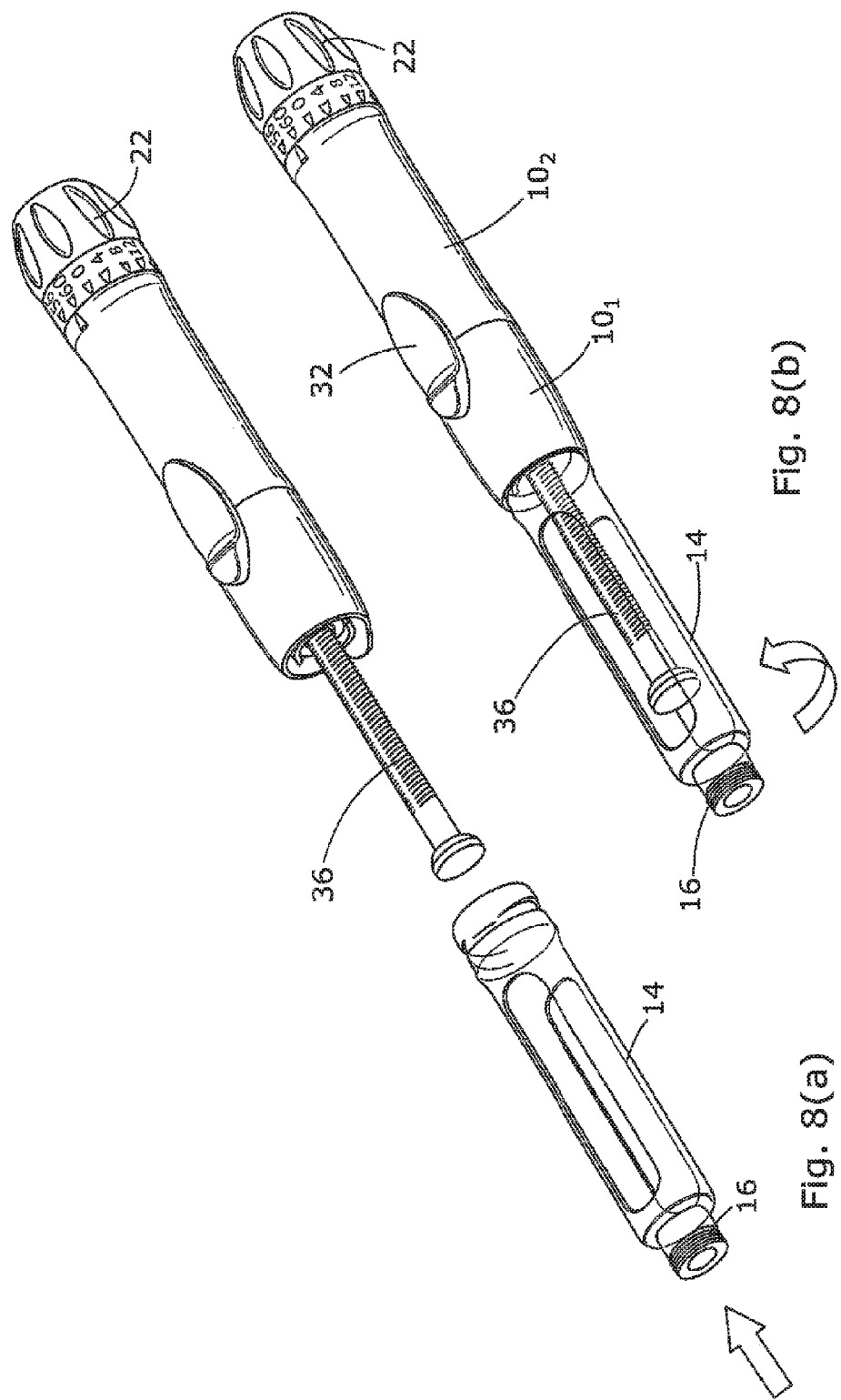

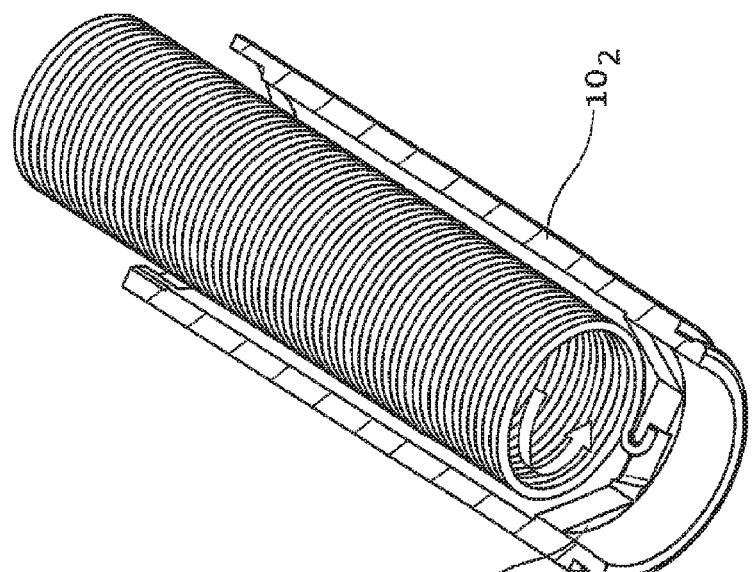
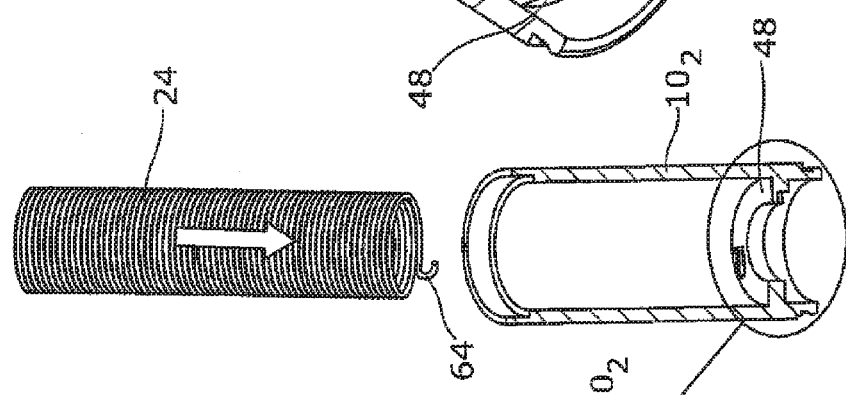
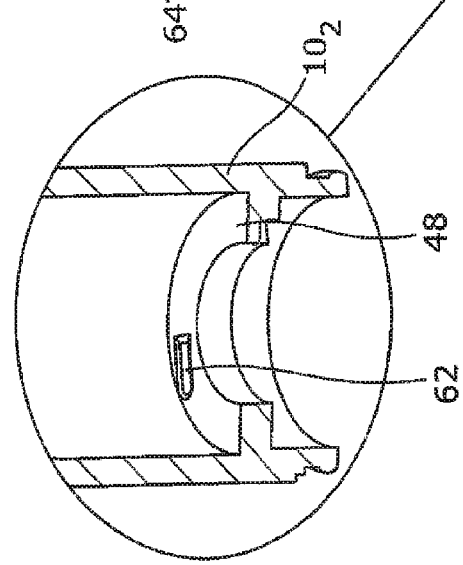
Fig. 9(a)
Fig. 9(b)
Fig. 9(c)

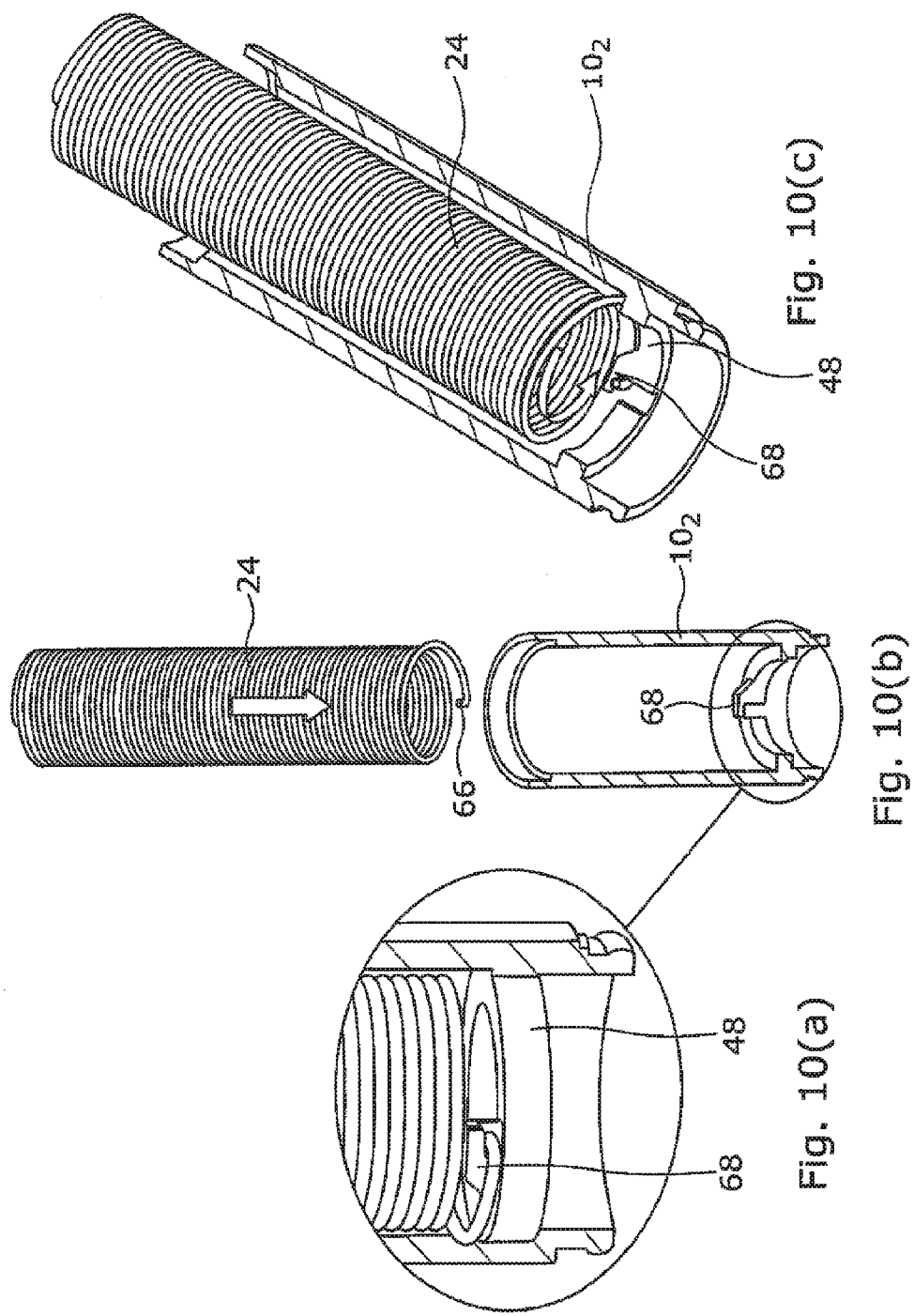

INJECTION DEVICE

BACKGROUND OF THE INVENTION

This invention relates to injection devices and methods of assembly thereof. In particular, but not exclusively, the invention relates to automatic or semi-automatic pen-type injectors where the user dials in a dose by rotating a ratcheted dose setting knob by a desired angular amount, thereby straining a torsion spring. On release of the ratchet, the consequent rotation causes expression of a dose of a preset volume. Typical examples of such devices include our widely available Autopen® pen injector and other injectors of the type described in U.S. Pat. No. 5,104,380.

In the assembly of such devices the introduction, alignment and securing of the torsion spring within the housing is normally done by hand because skill is required to achieve correct assembly. With the increasing numbers it is not cost-effective to assemble such devices by hand and so some form of automatic assembly is required. However, automatic assembly devices are not capable of assembling in the same manner as heretofore. A need exists for a spring anchorage which is well suited for automatic assembly, allowing rapid installation by an automated assembly machine.

SUMMARY OF THE INVENTION

Accordingly, in one aspect, this invention provides an injection device, comprising:

a housing for containing in use a syringe or cartridge of medicament;

a rotary drive shaft for being rotated by an adjustable preset amount to express a corresponding amount of medicament from said syringe or cartridge in use;

a torsion drive spring anchored at one end region relative to said drive shaft and at its other end region being secured to a fitting adapted to non-rotatably engage a seat on said housing.

The fitting may conveniently comprise a collar element, with the collar element and said seat being adapted to allow full engagement only at a single relative angular orientation.

The invention also extends to a method of attaching said drive spring to said housing in a device as set out above, which comprises providing respective complementary formations on said other end of the spring and a cooperating portion of the housing, inserting said spring into said housing and rotating said spring and said housing relative to each other thereby to secure said spring relative to said housing.

In one arrangement the complementary formation provided on said spring comprises a fitting, and said method comprises attaching said fitting to said drive spring before inserting said spring into said housing. The fitting may comprise a collar element.

Preferably said spring formation and said housing include complementary features whereby said fitting may be non-rotatably engaged in said housing.

Alternatively said formation may comprise an integrally formed portion on an end of said spring. Thus said formation may comprise a hooked portion, or e.g. a radially or axially projecting portion.

Where the spring formation is hooked or radially projecting the formation on the housing may comprise a hooked portion adapted to capture said portion of the spring when said spring is rotated.

In other arrangements, the formation on the spring may comprise a generally axially extending portion that can be introduced axially into an opening in a structural member associated with or forming part of the housing, the end region subsequently engaging or hooking around a feature associated with said aperture. In one such arrangement, a resiliently deformable longitudinally extending hooked arrangement is designed to be pushed axially through an aperture or slot integral with or associated with the housing and to engage an abutment adjacent said slot or aperture to retain that end of the spring. The hooked arrangement may be designed to contract as it passes through said slot or aperture and then to expand to allow it to grip the abutment.

In another arrangement an end portion of the spring extends rearwardly and, in assembly is pushed through a slot or aperture and then bent to retain that end of the spring.

In another aspect this invention provides an injection device comprising:

a housing for containing in use a syringe or cartridge of medicament;

a rotary drive shaft for being rotated by an adjustable preset amount to express a corresponding amount of medicament from said syringe or cartridge in use;

a torsion drive spring anchored at one end region to relative said drive shaft and, at its other end region being secured by means of respective complementary formations on said spring and said housing adapted rotatably to be engaged in use, and, following engagement, to prevent further rotation in the same sense.

We have also designed an arrangement to allow the dose setting knob to be rotated by close to or more than 360° without requiring complex spiral or threaded scales. Thus, in another aspect, this invention provides an injection device comprising:

a housing for containing in use a syringe or cartridge of medicament;

a drive mechanism disposed within said housing and comprising a spring-driven rotary drive shaft which during a dose setting routine is rotated against the force of the spring in a first sense from a rest position to a preset angular position to determine the magnitude of the dose subsequently to be expressed when said drive shaft is released to return to its rest position, characterised by a stop arrangement for limiting angular movement of said drive shaft in the return sense, said stop arrangement including an intermediate member mounted for angular movement within said housing, said intermediate member having a first abutment surface for cooperating with an abutment surface on said housing, and a second abutment surface for cooperating with an abutment surface on said drive shaft, whereby rotation in said return sense beyond the rest position is prevented.

Preferably, the accumulated angular rotation of said drive shaft relative to said intermediate member and said intermediate member relative to said housing is greater than 360°.

In another aspect, this invention provides an injection device comprising a drive mechanism including a rotary drive gear threaded onto a threaded drive plunger having a forward end and a rearward end, wherein the rearward end of said plunger is provided with a resiliently deformable end stop formation designed so that the rotary drive gear may be passed over the end stop formation in the forward direction for assembly, but once assembled said end stop formation limits forward threaded movement of said plunger with respect to said drive gear.

Whilst this invention has been described above, it extends to any inventive combination or sub-combination of the features disclosed herein.

BRIEF DESCRIPTION OF THE DRAWING FIGURES

Figure 12:
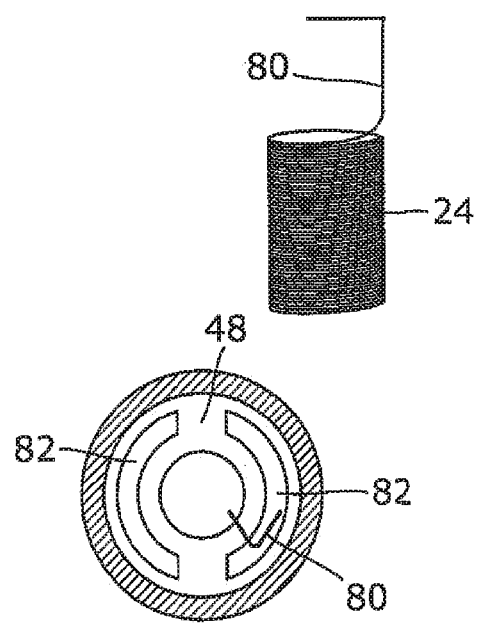

The invention may be performed in various ways and a number of embodiments will now be described by way of example only, reference being made to the accompanying drawings in which:

FIG. 1 is an exploded view of a first embodiment of pen injector in accordance with this invention;

FIGS. 2(a) to (c) are views showing assembly of the torsion spring with the spring locating disk;

FIGS. 3(a) to (f) are views showing assembly of the torsion spring and spring locating disk into the rearward drive housing part;

FIGS. 4(a) to (e) are views showing assembly of the drive shaft and intermediate stop disk into the rearward drive housing part;

FIGS. 5(a) to (e) are views showing assembly of the plunger, drive gear and trigger into a forward drive housing part;

FIGS. 6(a) and (b) are views showing connection of the forward and rearward drive housing parts;

FIGS. 7(a) to (d) are views showing setting of the preload in the torsion spring and securing of the dose setting knob;

FIGS. 8(a) and (b) are views showing securing of the cartridge housing to the remainder of the device to complete assembly;

FIGS. 9(a) to (c) are views showing assembly of a torsion spring into the rearward drive housing part in another embodiment;

FIGS. 10(a) to (c) are views showing assembly of the torsion spring into the rearward drive housing part in a further embodiment;

FIG. 11 is a schematic view showing assembly of the torsion spring into the rearward drive housing part in another embodiment, and FIG. 12 is a schematic view showing assembly of the torsion spring into the rearward drive housing part in yet another embodiment.

DETAILED DESCRIPTION OF THE INVENTION

The first embodiment of automatic pen injector is designed to have a low component count and to be specially adapted for ease of automated or semi-automated assembly. Referring to FIG. 1 and FIG. 8(b), the device when assembled comprises a drive housing 10 including forward and rearward drive housing parts $10_1$, $10_2$ and containing a drive mechanism indicated generally at 12. Connected to the forward end of the drive housing 10 is a cartridge housing 14 which houses a cartridge of medicament. A known form of double-ended pen tip needle (not shown) may be screwed onto the threaded portion 16 at the front of the cartridge housing. A cap 18 may be slid over the cartridge housing to protect the cartridge and its contents prior to use.

The operation of the device is essentially as described in our earlier U.S. Pat. No. 5,104,380. Thus, a ratcheted drive shaft 20 is rotated away from a rest position by twisting a dose setting knob 22 to dial in a required dose magnitude. Rotating the drive shaft 20 winds up a torsion spring 24 anchored at its forward end to the drive housing 10 and at its rearward end to the drive shaft 20. The forward end of the drive shaft 20 has a ratchet 26 which engages an inner toothed ratchet surface 28 on the inner circumference of a rearwardly directed annular flange of a drive gear 30 having a central threaded bore. The drive gear 30 is held stationary against rotation during the dose setting operation by its engagement with a trigger 32. Once the required dose has been dialled in and a pen tip applied to the cartridge housing, a dose may be expressed by pushing the trigger 32 forwardly against its integrally formed spring portion 34, thereby releasing the drive gear 30 so that the drive gear and drive shaft 20 rotate under the influence of the torsion spring 24 to return the drive shaft 20 to its rest position. The central bore of the drive gear 20 is threadedly engaged with a plunger 36 which has diametrically opposed longitudinal keyways 38 engaged by respective diametrically opposed keys 40 in the forward drive housing part $10_1$, so that rotation of the axially fixed drive gear 30 causes extension of the plunger 36 by a preset amount dependent on the dose dialled in, and the pitch of the thread.

The rear end of the plunger is provided with an integral resilient end stop formation 37 comprising a stem 39 and forwardly directed sprung arms 41 as seen in FIG. 5. The formation is designed so that the plunger can be introduced into the forward end of the drive gear, with the sprung arms 41 deflecting inwardly to pass through the threaded bore. Once assembled however the formation 37 acts as an end stop to limit forward threaded movement of the plunger 36 relative to the drive gear 30. In existing arrangements, this requires the plunger to have a separate end stop (or front pressure plate), which requires a separate moulding and a further assembly step.

Referring now particularly to FIGS. 2(a) to (c) and 3(a) to (f), in this arrangement, the forward end of the torsion spring 24 is provided with a hooked-back portion 42. A spring locating disk 44 is provided with spaced oppositely directed lugs 46 around one of which the hooked portion 42 of the spring may be hooked to assemble the spring to the disk, as shown in FIGS. 2(a) to 2(c). It will be noted that, for ease of assembly, the spring locating disk 44 is symmetric (i.e. it has two fold rotational symmetry about the diameter that passes between the lugs) so that it can be attached to the torsion spring in either of the two main orientations. The spring locating disk 44 includes a number of spaced flanges 47 around its periphery. The inner forward end of the rearward drive housing part is provided with an annular end wall 48 from the rear surface of which project a number of lugs 50 spaced with regard to the flanges of the spring locating disk so that the locating disk can only seat against the annular end wall 48 in a single angular orientation. In order to assemble the spring 24 into the rear drive housing part and to effect the anchorage of the spring relative to the housing, the spring, with its locating disk 44 attached, merely needs to be introduced longitudinally into the rearward drive housing to press the spring locating disk against the lugs 50, with the spring then being twisted to allow the disk to seat against the end wall in its predetermined angular position.

Referring now to FIG. 4, with the spring 24 and locating disk assembled together in the rear drive housing part $10_2$, the drive shaft 20 is passed through the central space of the spring, with a diametral folded rear end termination of the spring being seated in a slot in the rear of the drive shaft to anchor that end of the spring relative to the drive shaft. The extent of angular movement of the drive shaft, and thus the dose setting knob is limited in innovative fashion by providing a spigot 52 on the drive shaft 20 as previously, but which cooperates with an intermediate rotatable shuttle disk 54 which fits within the forward end of the rearward drive housing part $10_2$. The intermediate shuttle disk 54 has on its rearward side a spigot 56 that is received in a rebate 58 in the annular wall 48 which therefore allows the shuttle disk 54 to rotate from a rest position defined by one end of the rebate to a second position defined by the other end of the rebate (typically about 180°). Likewise, on its forward surface, the shuttle disk 54 has a rebate 60 which cooperates with the spigot 52 on the drive shaft 20 to allow movement between a stop position at one end of the rebate a wound position at the other end of the rebate (typically about 180°). In this manner, the drive shaft may be rotated to give a full 360° of rotation as the shuttle disk can rotate 180° with respect to the forward housing and the drive shaft can rotate 180° relative to the shuttle disk, with these two angular distances accumulating to provide the 360° rotation. This is achieved without compromising the robustness of the stops. It is also achieved without requiring threaded scales or the like which require complex mouldings.

Referring now to FIG. 5, the forward end of the device is assembled by aligning the keyways 38 on the plunger 30 with the keys 40 in the forward drive housing part 10, and sliding the plunger 30 into engagement with the housing part. The trigger button 32 is inserted into the housing part and the drive gear 30 then threaded onto the rear end of the plunger 30, snapping it past the end stop formation 37, and running it up the threads to a predetermined start position.

As shown in FIGS. 6(a) and (b) the forward housing $10_1$ is then snapped onto the rear housing $10_2$ by a snap fit. This action causes the front end of the drive shaft to enter into the drive gear and for the ratchet to engage, but with the torsion spring unstrained. Next, the drive shaft is rotated as shown in FIG. 7(a) to apply the required preload to the torsion spring. The spring is held against rotation at its front end by the spring locating disk. The forward end of the drive shaft rotates relative to the drive gear in ratchet fashion, with the drive gear being held against rotational movement by the trigger. Having applied the preload, the dose setting knob is aligned such that the zero mark lines up with the arrow on the housing and then snap fitted onto the end of the drive shaft. The cartridge housing is then attached to the front end of the drive housing by suitable coupling action such as snap fit, screw thread or bayonet as shown in FIGS. 8(a) and (b).

Referring now to FIGS. 9(a) to (c), in an alternative embodiment, instead of using a separate spring locating disk 44, an internal annular wall 48 in the forward part of the rearward drive housing is provided with an opening 62 designed to capture and seat a spring hook 64 on the forward end of the torsion spring 24 when the torsion spring is introduced longitudinally into the housing and rotated.

In a yet further embodiment, shown in FIGS. 10(a) to (c), the tip of the spring is bent through 90° to provide a radially inwardly extending spring latch 66, and an internal annular wall 48 within the rearward drive housing is provided with an upstanding catch 68 designed to capture and seat the spring when the spring is introduced into the housing and rotated.

In each of the above two arrangements the spring is secured by introducing the spring longitudinally and rotating it relative to the housing. In other arrangements the spring may be secured by deforming an end region either permanently (plastic deformation) or temporarily in a snap action (resilient deformation). For example the end of the spring may be secured by inserting longitudinally so that the end region passes through an aperture and subsequently is retained thereby. In one example, as shown in FIG. 11, the rear end of the spring is folded over to provide a loop 70 with an out-turned end 72 similar to a hair grip. The loop is dimensioned so that the arched rear portion 74 can be pushed through an aperture 76 in a bulkhead 48 or other housing structure with the out-turned end flexing to snap through the aperture and then recovering its shape to grip an abutment 78 adjacent the aperture when pulled forwardly, to locate the spring 24 securely relative to the housing.

FIG. 12 shows another example in which the spring 24 has an axial portion 80 at its rear end which during assembly is pushed through one or two slots 82 provided in a bulkhead 48 or similar structure and then bent over into the other slot.

The invention claimed is:

1. An injection device, comprising:
   a housing for containing a syringe or cartridge of medicament;
   a rotary drive shaft for being rotated by an adjustable preset amount to cause expression of a corresponding amount of medicament from said syringe or cartridge in use; and
   a torsion drive spring i) at a first end region anchored relative to said drive shaft and, ii) at an opposite, second end region secured to a fitting adapted to non-rotatably engage a seat on said housing.

2. An injection device according to claim 1, wherein said fitting comprises a collar element, with the collar element and said seat being adapted to allow full engagement only at a single relative angular orientation.

3. A method of attaching a drive spring, comprising:
   with an injection device comprising a housing for containing in use a syringe or cartridge of medicament, a rotary drive shaft for being rotated by an adjustable preset amount to express a corresponding amount of medicament in use, and a torsion drive spring anchored at a first end region relative to said drive shaft, non-rotatably anchoring an opposite, second end to said housing by
   i) providing respective complementary formations on said second end of the drive spring and a cooperating portion of the housing,
   ii) inserting said second end of the drive spring into said housing, and
   iii) rotating said drive spring and said housing relative to each other to engage a) the complementary formation on the drive spring with b) the complementary formation on the housing to thereby non-rotatably anchor said second end of the said drive spring relative to said housing.

4. A method according to claim 3, wherein the complementary formation provided on said drive spring comprises a fitting, and said method comprises attaching said fitting to said drive spring before inserting said drive spring into said housing.

5. A method according to claim 4, wherein said formation and said housing include complementary features whereby said fitting may be non-rotatably engaged in said housing.

6. A method according to claim 5, wherein said fitting comprises a collar element.

7. A method according to claim 3, wherein said spring formation comprises an integrally formed portion on an end of said drive spring.

8. A method according to claim 7, wherein said spring formation comprises a hooked portion.

9. A method according to claim 8, wherein said spring formation comprises a radially projecting portion.

10. A method according to claim 9, wherein the formation on the housing comprises a hooked portion adapted to capture said radial portion of the drive spring when said drive spring is rotated.

11. An injection device, comprising:
    a housing for containing a syringe or cartridge of medicament in use;
    a rotary drive shaft for being rotated by an adjustable preset amount to cause expression of a corresponding amount of medicament from said syringe or cartridge in use;
    a torsion drive spring i) at a first end region anchored relative to said drive shaft and, ii) at an opposite, second end region being adapted to non-rotatably engage a seat on said housing by means of respective complementary formations on said drive spring and said housing arranged rotatably to be engaged in use, and, following engagement, to prevent further rotation in a same direction.

12. A method of attaching a drive spring, comprising:
    with an injection device comprising a housing for containing in use a syringe or cartridge of medicament, a rotary drive shaft for being rotated by an adjustable preset amount to express a corresponding amount of medicament in use, and a torsion drive spring anchored at a first end region relative to said drive shaft, non-rotatably anchoring an opposite, second end region with respect to said housing by i) providing a formation on said second end of the drive spring,
ii) introducing said second end of the drive spring into said housing to pass said formation through an aperture or slot associated with said housing, and
iii) hooking said formation around a cooperating portion of the housing to engage a) said formation with b) the cooperating portion of the housing to thereby non-rotatably anchor said second end of said drive spring relative to said housing.

13. An injection device, comprising:

a housing for containing a syringe or cartridge of medicament in use;

a rotary drive shaft for being rotated by an adjustable preset amount to cause expression of a corresponding amount of medicament from said syringe or cartridge in use; and a torsion drive spring i) at a first end region anchored relative to said drive shaft and, ii) at an opposite, second end region having a formation that is passable through an aperture or slot associated with said housing, the formation being hookable around a cooperating portion of said housing thereby to non-rotatably anchor said drive spring relative to said housing.

\* \* \* \* \*